United States Patent
Hampp et al.

(10) Patent No.: US 11,065,015 B2
(45) Date of Patent: Jul. 20, 2021

(54) NAVIGATED PATELLA CLAMP

(71) Applicant: Howmedica Osteonics Corp., Mahwah, NJ (US)

(72) Inventors: Emily Hampp, Far Hills, NJ (US); John R. Fossez, Frisco, TX (US); Michael C. Ferko, Warwick, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 224 days.

(21) Appl. No.: 16/352,268

(22) Filed: Mar. 13, 2019

(65) Prior Publication Data

US 2019/0209187 A1 Jul. 11, 2019

Related U.S. Application Data

(63) Continuation of application No. 15/087,202, filed on Mar. 31, 2016, now Pat. No. 10,314,599.

(51) Int. Cl.
| | |
|---|---|
| *A61B 17/15* | (2006.01) |
| *A61B 34/20* | (2016.01) |
| *A61B 17/17* | (2006.01) |
| *A61B 90/00* | (2016.01) |

(52) U.S. Cl.
CPC ........ *A61B 17/1767* (2013.01); *A61B 17/158* (2013.01); *A61B 34/20* (2016.02); *A61B 2034/2072* (2016.02); *A61B 2090/3983* (2016.02)

(58) Field of Classification Search
CPC ................ A61B 17/1767; A61B 34/20; A61B 2034/2072; A61B 17/158
See application file for complete search history.

(56) References Cited

U.S. PATENT DOCUMENTS

| | | | |
|---|---|---|---|
| 4,633,862 A * | 1/1987 | Petersen | A61B 17/158 606/211 |
| 4,896,661 A | 1/1990 | Bogert et al. | |
| 5,122,130 A | 6/1992 | Keller | |
| 5,147,365 A * | 9/1992 | Whitlock | A61B 17/158 606/88 |
| 6,010,509 A * | 1/2000 | Delgado | A61F 2/461 606/88 |
| 6,261,296 B1 | 7/2001 | Aebi et al. | |
| 6,712,825 B2 | 3/2004 | Aebi et al. | |

(Continued)

FOREIGN PATENT DOCUMENTS

EP 1574171 A1 9/2005

*Primary Examiner* — Zade Coley
(74) *Attorney, Agent, or Firm* — Lerner, David, Littenberg, Krumholz & Mentlik, LLP (57) ABSTRACT

Disclosed herein are systems and methods of patella arthroplasty. A navigated patella clamp used in an arthroplasty procedure includes first and second movable jaw members and an actuation member coupled to the first and second jaw members for moving the first and second jaw members along a plane toward and away from one another. The patella clamp further includes a tracker and adjustable stylus for positioning the clamp on a patient's patella below a desired resection plane. The adjustable stylus coupled to the clamp is used to check the position and orientation of the clamp with respect to the patella to ensure the correct amount of bone will be resected from the patella corresponding to the thickness of a patella component that will be implanted on the resected patella.

19 Claims, 8 Drawing Sheets

(56) References Cited

U.S. PATENT DOCUMENTS

| | | |
|---|---|---|
| 6,856,828 B2 | 2/2005 | Cossette et al. |
| 7,182,767 B2 * | 2/2007 | Canonaco ............ A61B 17/155 606/89 |
| 7,377,924 B2 * | 5/2008 | Raistrick ............. A61B 17/154 606/87 |
| 7,618,421 B2 | 11/2009 | Axelson, Jr. et al. |
| 7,632,279 B2 * | 12/2009 | Bastian ............... A61B 17/158 606/105 |
| 7,840,253 B2 * | 11/2010 | Tremblay ............ A61B 90/36 600/424 |
| 8,571,637 B2 | 10/2013 | Sheffer et al. |
| 8,728,087 B2 * | 5/2014 | Soliman ............. A61B 17/1767 606/88 |
| 2002/0068942 A1 | 6/2002 | Neubauer et al. |
| 2004/0162561 A1 * | 8/2004 | Marchyn ............ A61B 17/1677 606/78 |
| 2006/0052792 A1 | 3/2006 | Boettiger et al. |
| 2006/0084867 A1 * | 4/2006 | Tremblay ............. A61B 34/20 600/434 |
| 2006/0142777 A1 * | 6/2006 | Bastian ............... A61B 17/158 606/88 |
| 2008/0154262 A1 * | 6/2008 | Brundobler .......... A61B 90/50 606/53 |
| 2009/0062869 A1 * | 3/2009 | Claverie ............. A61B 90/50 606/324 |
| 2010/0222781 A1 | 9/2010 | Collazo et al. |
| 2010/0222782 A1 | 9/2010 | Collazo et al. |
| 2012/0095473 A1 * | 4/2012 | Soliman ............... A61B 17/158 606/88 |
| 2012/0101505 A1 * | 4/2012 | Claypool ............. A61B 17/158 606/88 |
| 2013/0079876 A1 * | 3/2013 | Fitz ..................... A61B 17/155 623/14.12 |

* cited by examiner

NAVIGATED PATELLA CLAMP

CROSS-REFERENCE TO RELATED APPLICATIONS

This application is a continuation of U.S. application Ser. No. 15/087,202, filed on May 31, 2016, the disclosure of which is incorporated herein by reference.

FIELD OF THE INVENTION

The present disclosure relates to a device used in aiding patella preparation and in particular relates to a navigated device that engages the patella in a planned position and orientation such that the patella may be resected in a desired manner.

BACKGROUND OF THE INVENTION

Patella preparation in total knee arthroplasty procedures is generally performed manually with the use of sawblades and clamps. Calipers may be used during preparation to contact opposing superior and inferior surfaces of the patella to aid in determining the depth of the cut. However, these conventional tools do not adequately control the depth and orientation of the cut which also results in the medial/lateral translational and rotational position of a patellar component.

Patella clamps may be used to clamp the anterior and articular surfaces of the patella before resecting the articular surface of the patella. Additionally, some patella clamps may require fixation pegs or keels to engage the patella before everting it to a desired angle. Common methods to remove bone from the articular surface of the patella include saw resection or milling/planar systems. The removal of bone in either of these systems may provide a flat, stable platform to support, but not secure, a prosthetic patellar component.

The patella includes boney landmarks such as the articular high point, retinaculum and/or the cartilage border. These landmarks may be referenced by a patella clamp to orient the clamp on the non-resected patella in view of a desired final placement of the patellar component. However, these landmarks are generally irregularly shaped, which makes it difficult to orient the clamp below a planned resection level.

BRIEF SUMMARY OF THE INVENTION

Disclosed herein are systems and methods for navigated patella preparation. A preoperative plan may be developed such that the patella may be intraoperatively prepared to receive an implant component in a desired position and orientation. The present invention includes a navigated clamp for use during the intraoperative bone resection.

In one method, a patella resection plane is preoperatively planned and the size of a patella component is preoperatively chosen as well as its position with respect to the resection plane. A patella and tracker instrument holder or clamp is provided which intraoperatively informs the surgeon where to place the clamp on the native patella such that the position and orientation of the resection plane can be made with either manual instrumentation or via a robotic cutting arm.

During preoperative planning, the patella resection plane and implant position are determined. Key boney landmarks of the patella are used in planning the patellar resection plane, which establish the coordinate system for positional alignment of the patella component. The component size and placement plan will consider the cartilage borders (both medially-laterally and superiorly-inferiorly), the articular high point and overall thickness of the patella to calculate size and placement of the patella component. The overall goal is to replicate patient patella thickness with the suggested component thickness. A graphics user interface ("GUI") will suggest a patella resection level based on the preoperative plan.

There is a correlation between the patella clamp and the registration tracker instrument. During preoperative planning, the positioning of the patella clamp must be determined to ensure its placement is below the resection plane or level. Intraoperatively, the system informs the surgeon of which stylus setting to use when placing and locking the patella clamp (correlated to patella component position). Also during the procedure, the surgeon places the patella clamp around the patella using the suggested stylus setting. The patella clamps houses a tracker for navigation, and the surgeon registers the patella bone by running a navigated probe across the bone to capture key landmarks. For example, the surgeon could surface map the articulating surface of the patella, the articulation high point, the retinaculum, and/or cartilage border. These landmarks preferably correlate back to the preoperative plan.

Once the patella is registered, the system knows the position of the patella relative to the tracker housed on the patella clamp. The GUI displays the final patella plan on the bone. A computer aided design ("CAD") model for the clamp is stored in the system software, so if the surgeon clamps above the resection level or there is a risk of machining the clamp, the system will prompt the surgeon to re-clamp and re-register. Once the clamp is sufficiently positioned and registered, the patella may then be resected using a cutting tool.

The clamp is designed to accommodate all size and shape patellae since there are two teeth per jaw which bite into the patella. The stylus has some built-in tolerance to ensure the patella is clamped below the level of resection and not in the machining path.

One aspect of the present invention is a patella clamp comprising first and second jaw members; an actuation member coupled to the first and second jaw members for moving the first and second jaw members along a plane toward and away from one another; a tracker; and an adjustable stylus.

In one embodiment of the first aspect, the first and second jaw members of the patella clamp each have at least one tooth for engaging a patella.

In another embodiment of the first aspect, the patella clamp further comprises first and second parallel support members coupled to the first and second jaw members respectively and the actuation member.

In yet another embodiment of the first aspect, the tracker is coupled to one of the first and second parallel support members.

In still yet another embodiment of the first aspect, the tracker is capable of receiving and transmitting digital information, the digital information relating to positing the patella clamp with respect to a patella.

In yet another embodiment of the first aspect, the adjustable stylus is coupled to one of the first and second jaw members.

In still yet another embodiment of the first aspect, the adjustable stylus is coupled to one of the first and second jaw members via a post, the stylus being adjustable about the post. In another embodiment, the post includes a plurality of grooves for adjust the stylus about the post, each of the plurality of grooves relating to a height of the stylus.

A second aspect of the present invention is a method of determining a position of a patella implant on a resected patella of a patient comprising displaying a three-dimensional model on a graphics user interface of an unresected patella of the patient; selecting a plurality of landmarks on the three-dimensional model including peripheral cartilage borders and an articular high point of the model; and determining a patellar resection plane on the model and a position of the patella implant with respect to the patellar resection plane.

In one embodiment of the second aspect, the peripheral cartilage borders include medial, lateral, superior and inferior borders. In another embodiment, the peripheral cartilage borders and articular high point are used to determine a thickness for the patellar implant.

In another embodiment of the second aspect, the peripheral cartilage borders and articular high point establish a coordinate system for positional alignment of the patellar implant.

In still yet another embodiment of the second aspect, the plurality of landmarks are used to calculate and suggest a location and an orientation of the patellar resection plane on the model.

In still yet another embodiment of the second aspect, the method further comprises positioning a patella clamp with respect to the determined patella resection plane, the navigated patella clamp having a tracker and a stylus. In another embodiment, the method further comprises engaging the unresected patella with first and second jaws of the patella clamp and a contact surface of the stylus.

In yet another embodiment, the first and second jaws engage the unresected patella adjacent the peripheral cartilage borders below the patellar resection plane. The contact surface of the stylus engages the articular high point of the unresected patella.

In still yet another embodiment of the second aspect, the method further comprises resecting the patella along the patellar resection plane and positioning the patella implant on the resected patella.

BRIEF DESCRIPTION OF THE DRAWINGS

Other objects and advantages of the present invention will be apparent from the following detailed description of the present preferred embodiments, which description should be considered in conjunction with the accompanying drawings in which like reference indicate similar elements and in which.

DETAILED DESCRIPTION

In describing preferred embodiments of the disclosure, reference will be made to the directional nomenclature used in describing the human body. It is noted that this nomenclature is used only for convenience and that it is not intended to be limiting with respect to the scope of the invention. When referring to specific directions in relation to a device, the device is understood to be described only with respect to its orientation and position during an exemplary application to the human body.

As used herein when referring to bones or other parts of the body, the term "proximal" means closer to the heart and the term "distal" means more distant from the heart. The term "anterior" means toward the front part or the face and the term "posterior" means toward the back of the body. The term "medial" means toward the midline of the body and the term "lateral" means away from the midline of the body.

Figure 1:
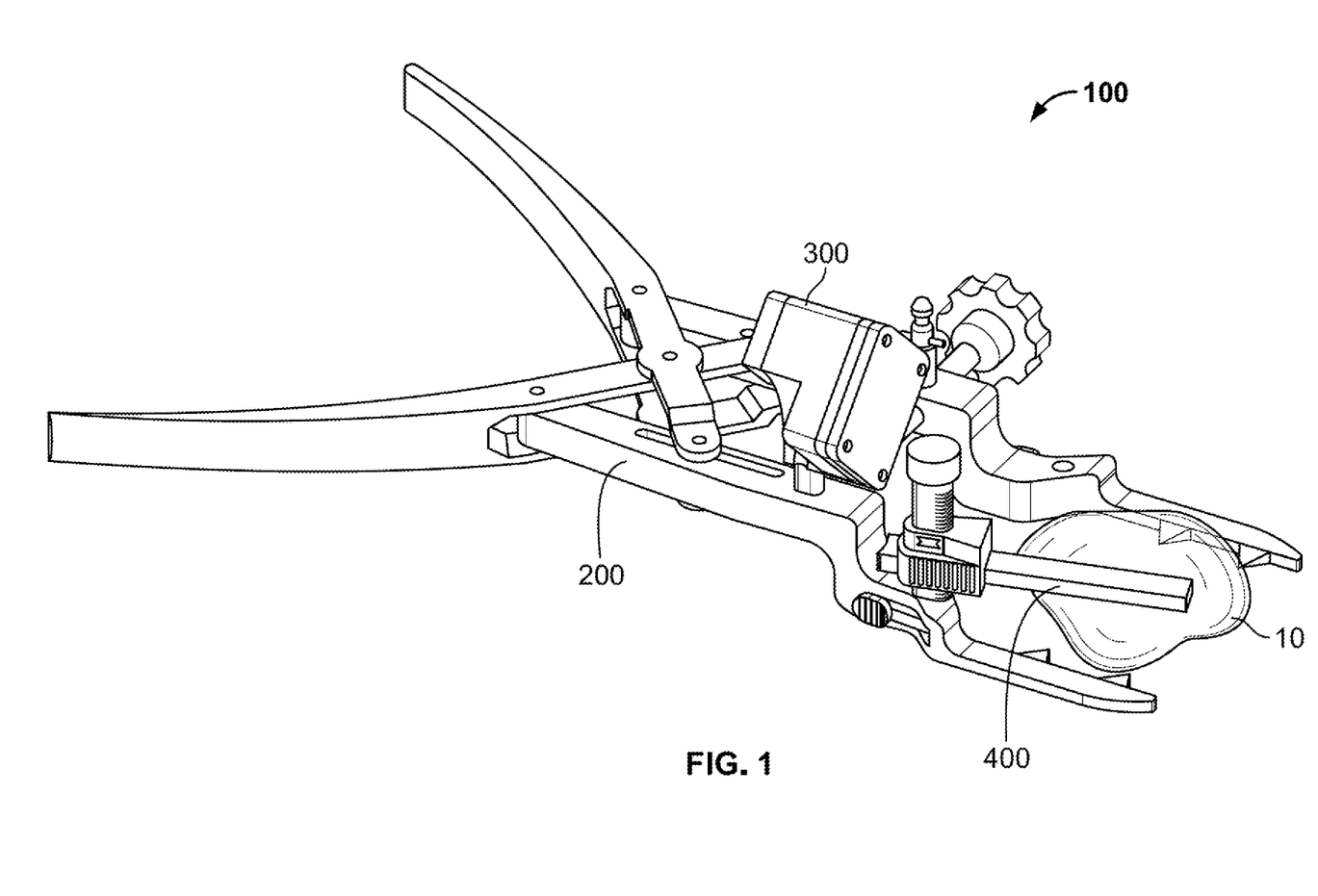
FIG. 1 is a perspective view of a navigated patella clamp of the present invention including a clamp, a tracker and an adjustable stylus.

FIG. 1 is a perspective view of a navigated patella clamp 100 of the present invention including a clamp 200, a tracker 300 and an adjustable stylus 400. Clamp 200 is shown engaged to an exemplary patella bone 10.

Figure 2:
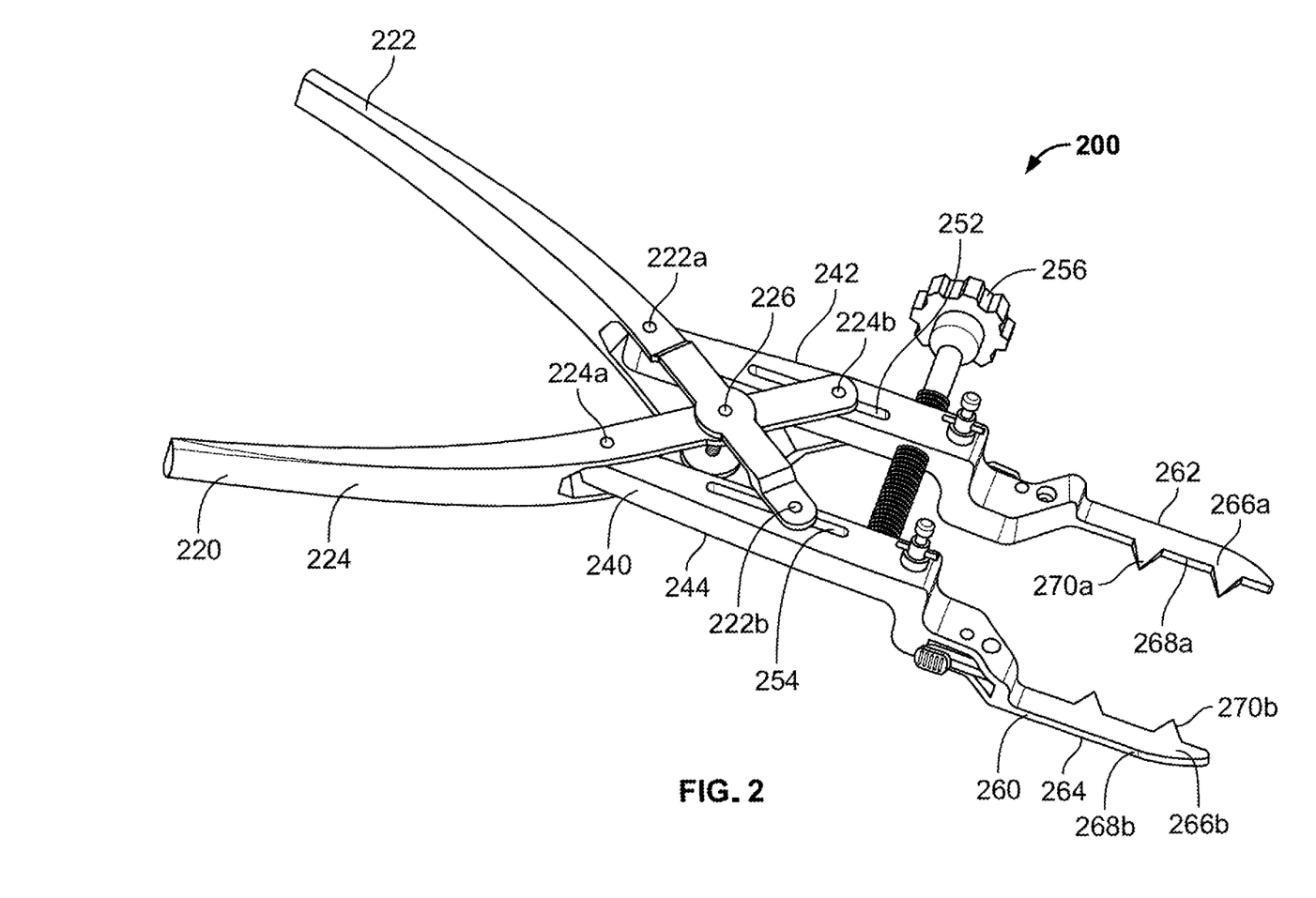
FIG. 2 is a perspective view of the clamp shown in FIG. 1.

FIG. 2 is a perspective view of clamp 200 shown in FIG. 1. Clamp 200 includes a handle portion 220, a parallel motion body portion 240 and a jaw portion 260. Handle portion 220 includes first and second pivotable handle members 222, 224. Each handle member 222, 224 includes first and second pin members 222a, 222b and 224a, 224b, respectively that allow the handle members 222, 224. A pin member 226 is coupled to both first and second handle members 222, 224. Pin members 222a, 222b, 224a, 224b, and 226 allow handle members 222, 224 to pivot toward and away from one another during use.

Parallel motion body portion 240 includes first and second arm portions 242, 244. Handle portion 222 is coupled at a distal portion of first arm portion 242 by first pin member 222a, while handle portion 224 is coupled at a distal portion of second arm portion 244 by first pin member 222b. Handle portion 222 is coupled to second arm portion 244 by second pin member 222b which may translate about a slot 254 in second arm portion 244, while handle portion 224 is coupled to first arm portion 242 by second pin member 224b which may translate about a slot 252 in first arm portion 242. First and second pin members 222b, 224b may translate in both linear proximal and distal directions within slots 254, 252 respectively. As handle portions 222, 224 are brought closer to one another, pin members 222b, 224b generally translate in a proximal direction about slots 252, 254 respectively. As handle portions 222, 224 are allowed to move away from one another, pin members 222b, 224b generally translate in an opposite distal direction about slots 252, 254 respectively.

Clamp 200 further includes a thumbwheel 256 with a threaded shaft 258. Threaded shaft 258 is threaded at least partially into opposing apertures in first and second arm portions 242, 244. As thumbwheel 256 is rotated in a clockwise direction, first and second parallel arm portions 242, 244 are brought closer together. As thumbwheel 256 is rotated in a counterclockwise direction, first and second parallel arm portions 242, 244 may be separated further away from one another.

Extending from body portion 240 of clamp 200 is jaw portion 260. Extending from first and second arm portions 242, 244 of body portion are respective first and second jaws 262, 264 of jaw portion 260. Jaws 262, 264 each have respective superior surfaces 266a, 266b and inferior surfaces 268a, 268b. Each jaw 262, 264 includes one or more respective teeth portions 270a, 270b. Jaws 262, 264 move toward and away from one another as either handle members 222, 224 are moved toward and away from one another and/or thumbwheel is rotated in a clockwise or counterclockwise direction respectively.

Figure 3:
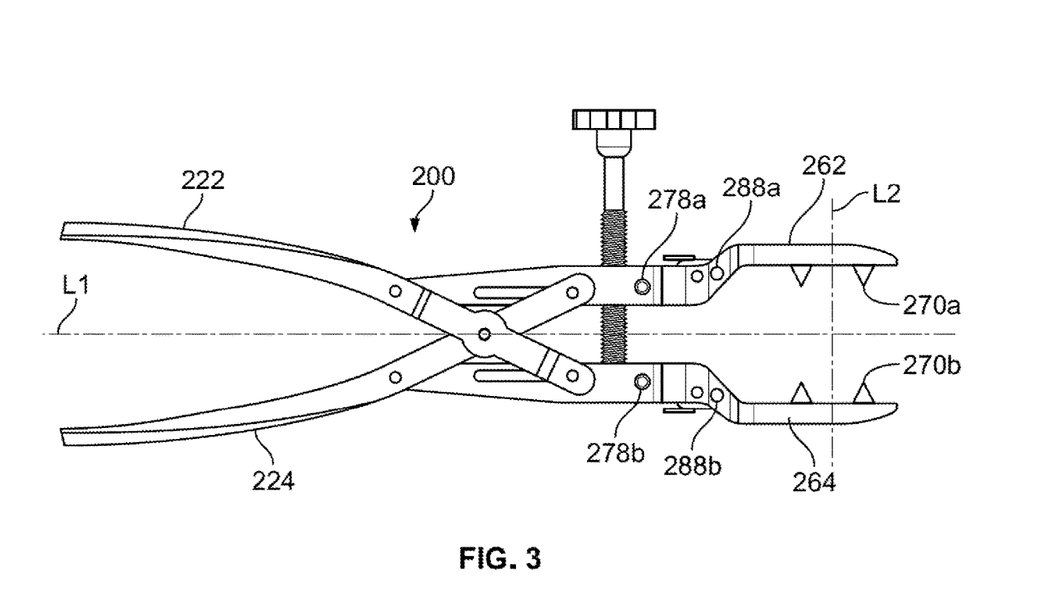
FIG. 3 is a top view of the clamp shown in FIG. 2.

Handle members 222, 224 and jaws 262, 264 move toward and away from longitudinal axis L1 of clamp 200 shown in FIG. 3 as clamp 200 is actuated either via handles 222, 224 and/or thumbwheel 256. Clamp 200 engages a patella bone such as patella 10 in FIG. 1, for example, such that teeth portions 270a, 270b of jaws 262, 264 engage outer surface portions of patella 10 about longitudinal axis L2. Depending on the orientation of clamp 200 with respect to the patella, teeth portions 270a, 270b may engage respective medial and lateral portions or proximal and distal portions of patella 10. In reference to patella 10, the term "superior" is used to reference an upper or outer portion of the bone while the term "inferior" is used to reference a bone contacting, articulating or inner portion of the bone. In this context, the terms "superior" and "anterior" are generally synonymous while "inferior" and "posterior" are generally synonymous.

Figure 4:
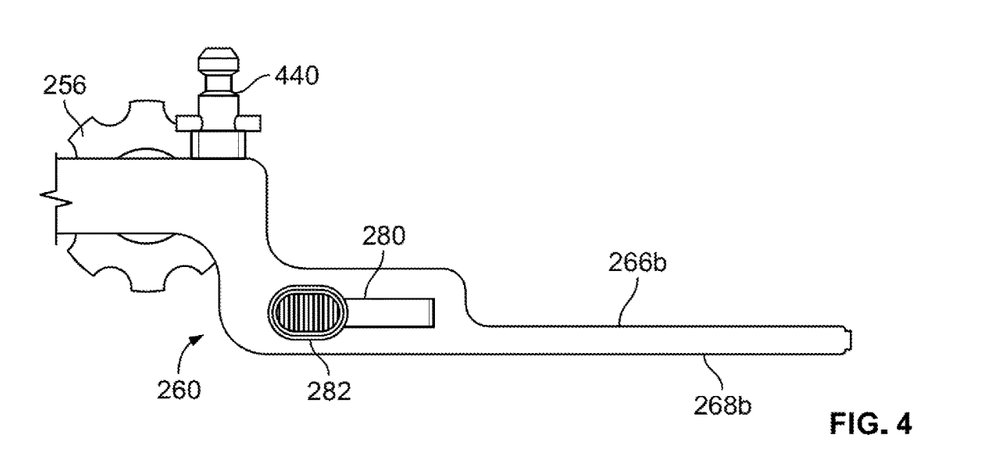
FIG. 4 is an enlarged side view of a jaw portion of the clamp shown in FIG. 2.

FIG. 4 shows an enlarged side view of jaw portion 260 of clamp 200. A tracker post 440 is shown coupled to clamp 200 with at least a portion thereof received in an aperture 278a, 278b in the parallel motion body portion 240. A release mechanism 280 is shown located on each jaw 262, 264 of jaw portion 260. Release mechanism 280 has a neutral locked position. A user can pull-back on contact surface 282 to move release mechanism 280 in a distal direction. Release mechanism is moved into an unlocked position when moved distally. Any known mechanism to provide force on release mechanism 280 proximally or into the neutral locked position can be used such as a spring, for example. When release mechanism 280 is a neutral position, apertures 288a, 288b on jaw portion 260 are slightly closed or a portion of release mechanism 280 is located within these apertures such that a post within these apertures would be captured and unable to move unless release mechanism 280 was moved distally.

Figures 5, 6:
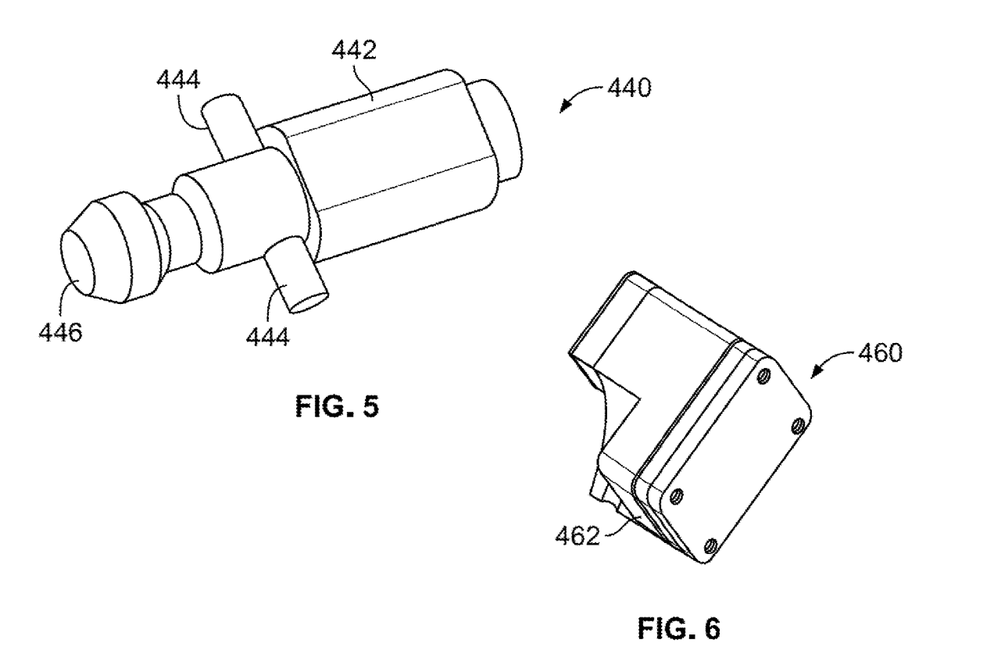
FIG. 5 is a perspective view of a tracker post of the clamp shown in FIG. 1.
FIG. 6 is a perspective view of the tracker shown in FIG. 1.

FIG. 5 is a perspective view of tracker post 440 having a body portion 442, arm portions 444 and a head portion 446. Body portion 442 is configured to be received at least partially within either one of apertures 278a, 278b of clamp 200. Arm portions 444 and head portion 446 are configured to engage corresponding recesses 462 within tracker 460 shown in FIG. 6. Tracker 460 may be engaged to tracker post in at least four positions with respect to a longitudinal axis L3 of tracker post 440. Each of the four positions are separated preferably 90° about the longitudinal axis of tracker post 440. In some embodiments, tracker 460 may rotate together with tracker post 440 with respect to apertures 278a, 278b. The location of tracker post 440 and the size of tracker 460 is such that movement of tracker 460 does not interfere with stylus 400 and vice versa. FIGS. 8A-8D are perspective views of tracker 460 in four orientations at least 90° different that one another about longitudinal axis L3 of tracker post 440. In each configuration, there is clearance between an outer surface of tracker 460 and stylus 400.

Figure 7:
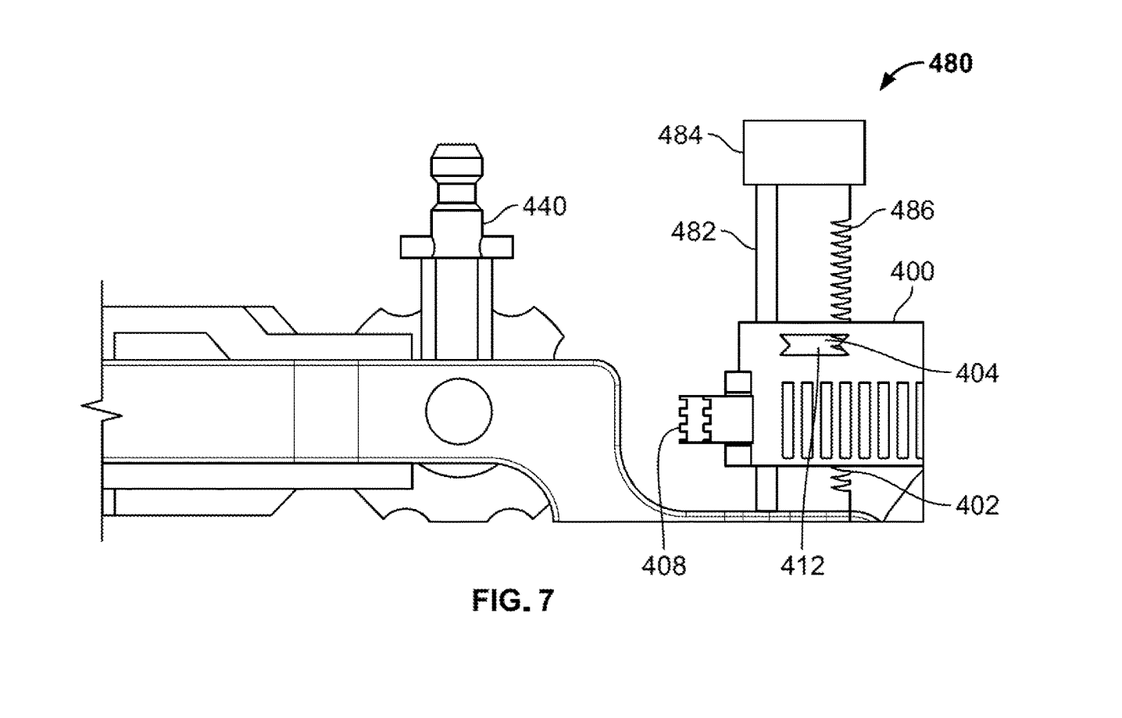
FIG. 7 is an enlarged side view of an intermediate portion of the clamp shown in FIG. 1 in which the adjustable stylus is shown in at a certain setting.
Figure 8A:
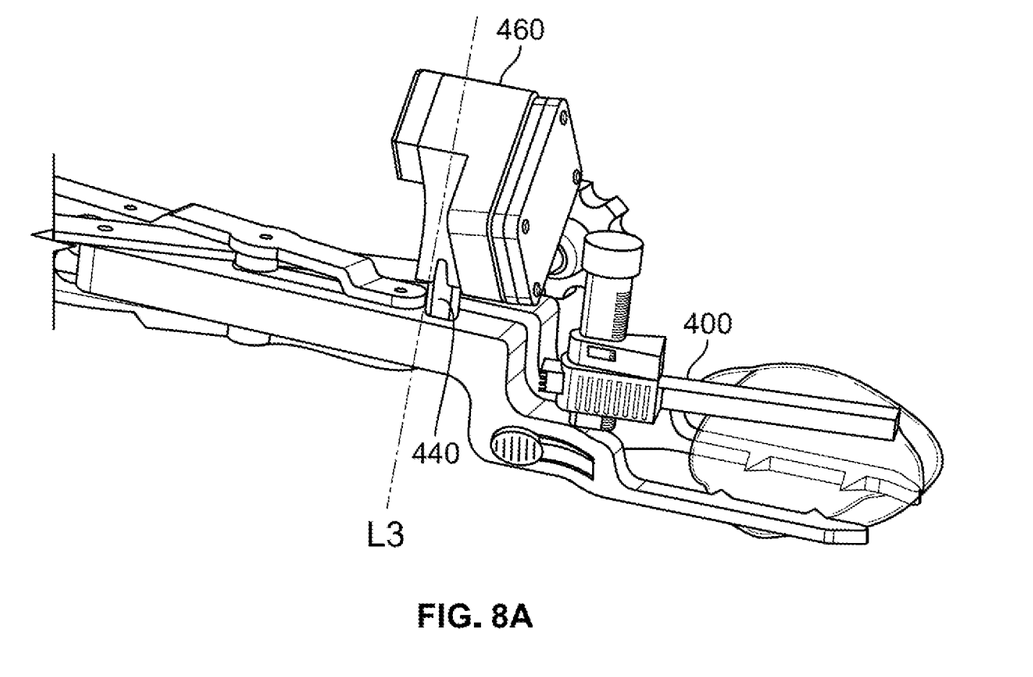
FIGS. 8A-8D are perspective views of the tracker of the navigated patella clamp of FIG. 1 in four orientations at least 90 degrees different that one another about a longitudinal axis of the tracker post.
Figure 8B:
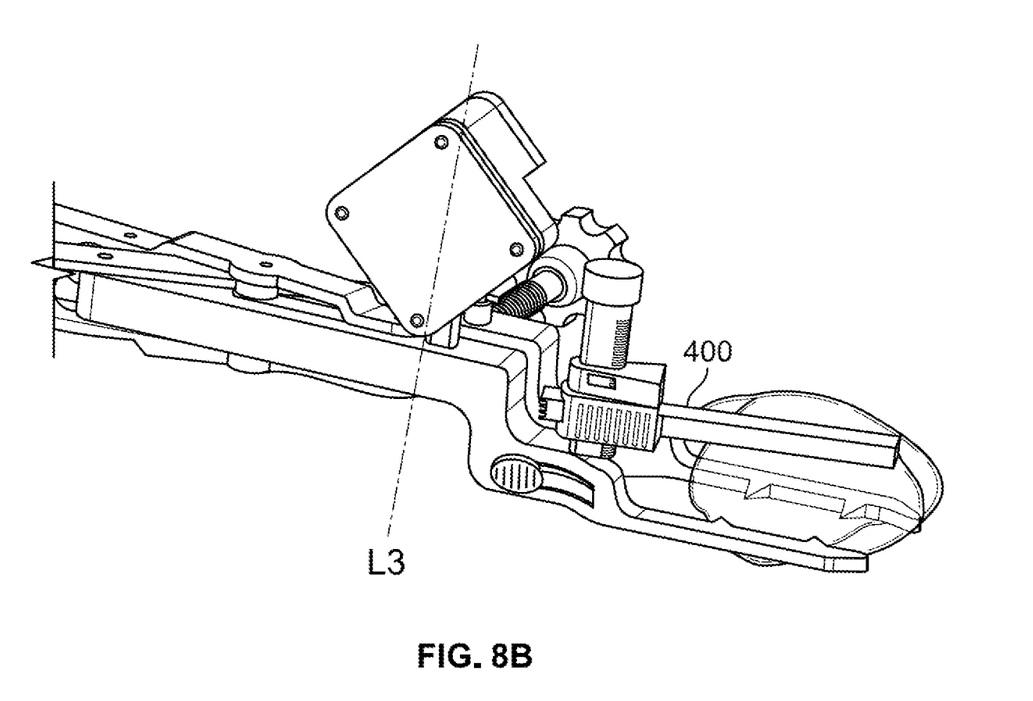
Figure 8C:
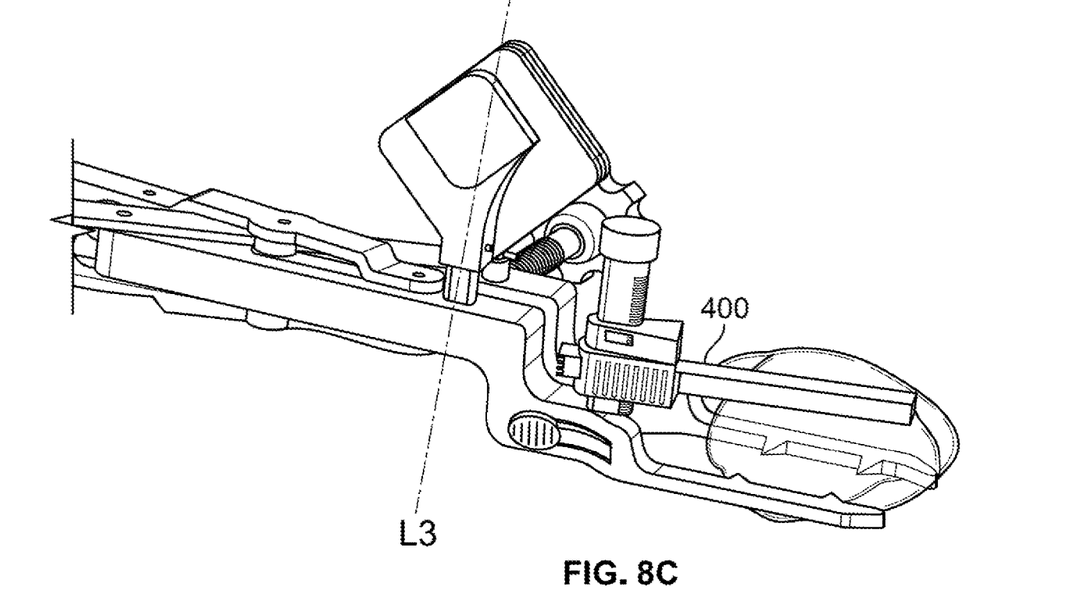
Figure 8D:
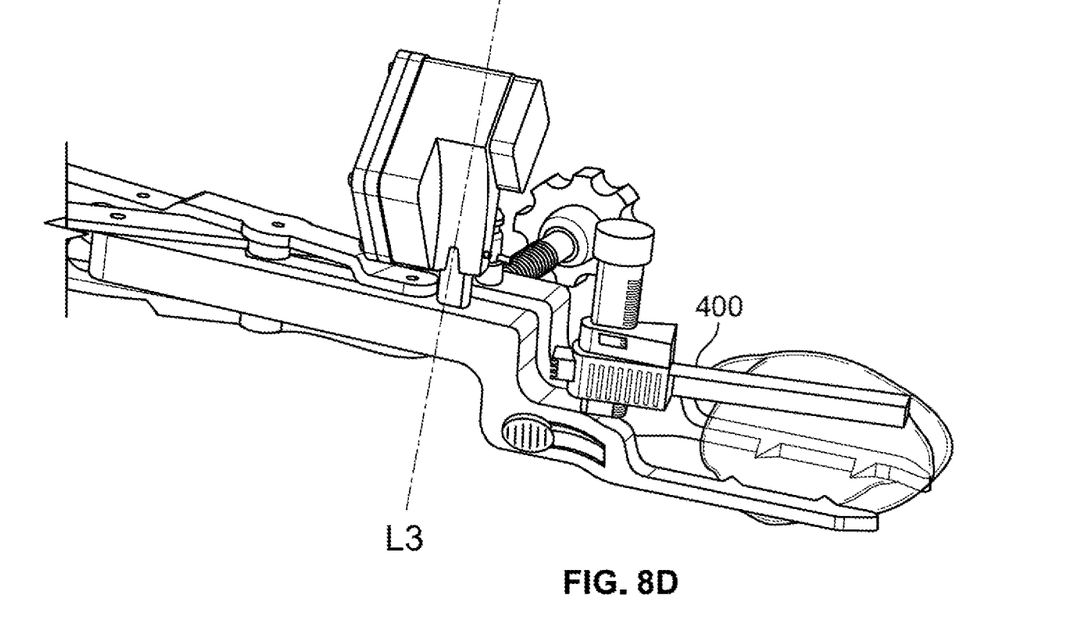

As shown in FIG. 7, a stylus post 480 is coupled to aperture 288b of clamp 200. Stylus post 480 includes a body portion 482 and a cap portion 484. Body portion 482 includes a plurality of teeth portions 486 along a length thereof. Stylus 400 has a bore 402 including a plurality of grooves 404 corresponding to the plurality of teeth portions 486 of stylus post 480. A release button 408 can activated to release the engagement between plurality of grooves 404 corresponding to the plurality of teeth portions 486 of stylus post 480. When release button 408 is activated, stylus 400 can be slid up and down the length of body portion 482 of stylus post 480 until the release button 408 is released to re-engage the grooves 404 and teeth portions 486.

Figure 9A:
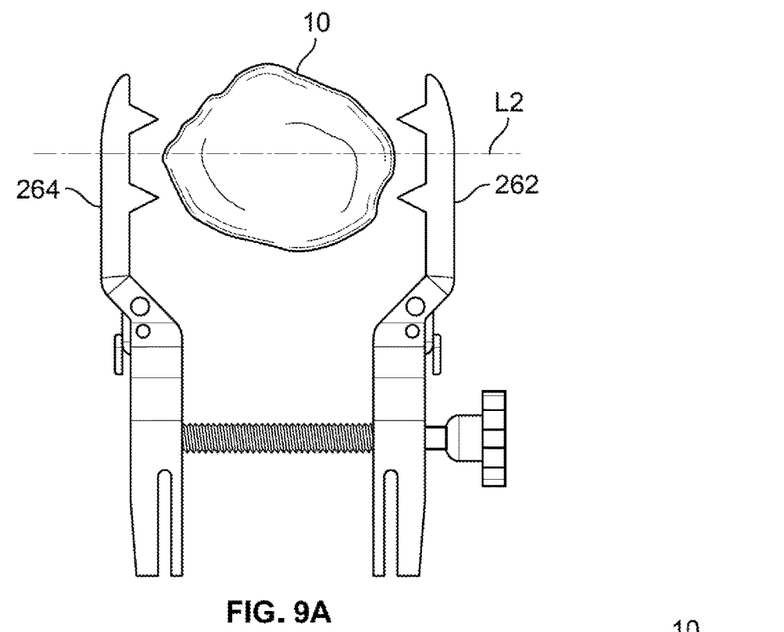
FIG. 9A shows the jaw end of the clamp of FIG. 2 oriented with respect to a patella in a medial to lateral direction in which the jaws are separated a maximum distance from one another.
Figure 9B:
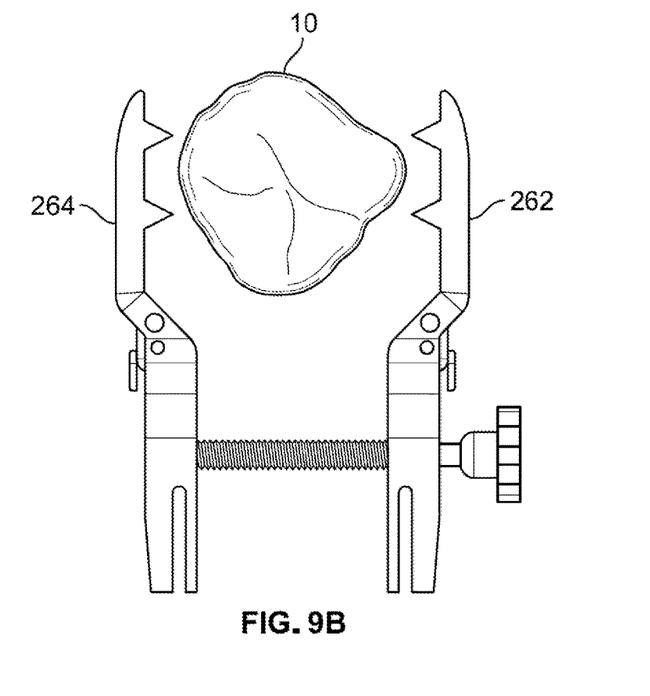
FIG. 9B shows the jaw end of the clamp of FIG. 2 oriented with respect to a patella in a superior to inferior direction in which the jaws are separated a maximum distance from one another.
Figure 9C:
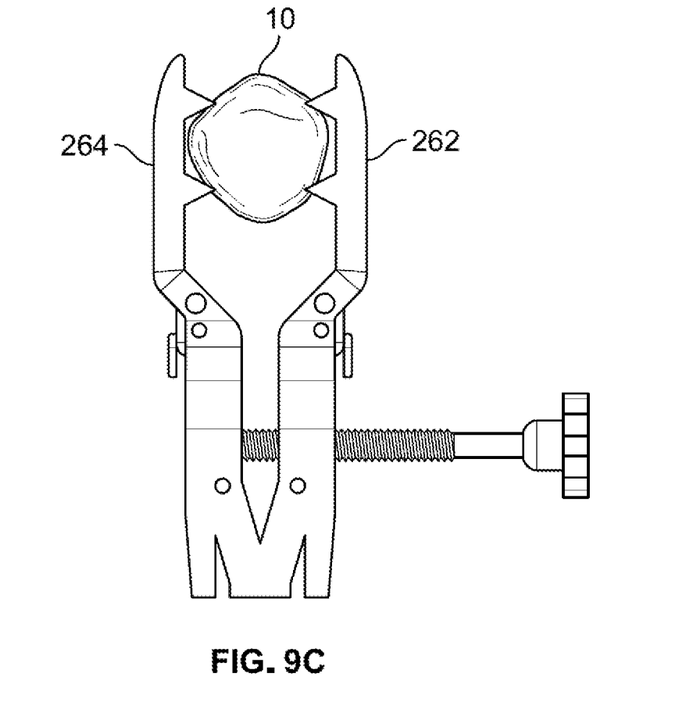
FIG. 9C shows the jaw end of the clamp of FIG. 2 oriented with respect to a patella in both medial to lateral and superior to inferior directions in which the jaws are separated a minimum distance from one another.

FIGS. 9A-9C show various positions of jaws 262, 264 with respect to patella 10. In FIG. 9A, jaws 262, 264 of clamp 200 are shown oriented with respect to patella 10 in a medial to lateral direction in which jaws 262, 264 are separated a maximum distance from one another about L2. FIG. 9B shows jaws 262, 264 oriented with respect to patella 10 in a superior to inferior direction in which jaws 262, 264 are separated a maximum distance from one another. FIG. 9C shows jaws 262, 264 fully engaged to patella 10 in both medial to lateral and superior to inferior directions such that jaws 262, 264 are separated a minimum distance from one another. It should be understood that patella 10 in reference to these maximum and minimum distances is only exemplary and that the location of jaws 262, 264 with respect to a patella being operated on will ultimately be based on the size and shape of that patella.

Figure 10:
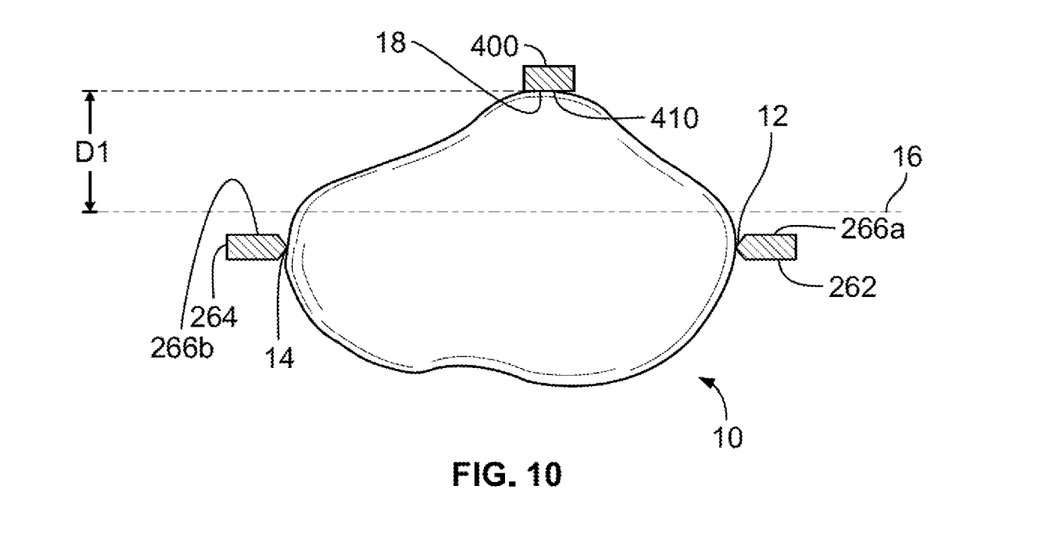
FIG. 10 is a front view of the jaws of a navigated patella clamp engaged to medial and lateral portions of a patella showing a resection level and an articular high point representing a corresponding high point of a patella component that will be implanted on the resected patella.

FIG. 10 is a front view of jaws 262, 264 of a navigated patella clamp engaged to medial and lateral portions 12, 14 of patella 10 showing a resection level 16 and an articular high point 18 representing a corresponding high point of a patella component (not shown) that will be implanted on the resected patella. The patella includes boney landmarks such as articular high point 18, retinaculum and/or the cartilage border. These landmarks are generally used in what may be referred to as a bony landmark patella positioning plan. During the pre-operative planning of patella positioning, these landmarks help in determining a position and orientation of the patella implant based on the alignment methodology used for orienting other implants in a TKA procedure, such as a femoral and/or tibial implant. These landmarks may also be used to orient patella clamp 200 on the non-resected patella 10 in view of a desired final placement of the patellar component. Patella clamp 200 positioning preferably utilizes stylus 400 for setting depth and the actual cartilage boarders for setting the angle of the clamp 200. These reference points help to ensure clamp 200 is not placed where the planned resection plane is, mitigating the need to reposition clamp 200 and re-register.

During preoperative planning, the size and orientation of a patellar component is taken into consideration when defining resection level 16. The position of jaws 262, 264 with respect to patella 10 is defined such that superior surfaces 266a, 266b of jaws 262, 264 will be oriented such that each is preferably parallel to resection level 16. The position of superior surfaces 266a, 266b below resection level preferably takes into account the cutting tool that will be used to resect patella 10 such that there is sufficient clearance that the cutting tool can function without contacting superior surfaces 266a, 266b while also allowing teeth 270a, 270b of jaws 262, 264 to sufficiently purchase bone of patella 10 and stabilize clamp 200 with respect to bone during patella resection.

A linear distance D1 as shown in FIG. 10 between a bottom surface 410 of stylus 400 and superior surfaces 266a, 266b is defined in the preoperative plan. Once this linear distance is calculated, the distance preferably corresponds to a specific tooth portion 486 and groove 404 of stylus 400. A viewing window 412 allows a user to see the position of stylus 400 with respect to the teeth portions 486 of stylus post 480. Stylus 400 is positioned along stylus post 480 according to the determined position from the preoperative plan. Stylus 400 is designed to not only move linearly about stylus post 480 but also rotationally in order to position with respect to articular high point 18. Stylus 400 is preferably rotated about a longitudinal axis of stylus post 480 until bottom surface 410 lies just above articular high point 18. Jaws 262, 264 are then oriented into position via tracker 460 and into contact with patella 10 such that superior surfaces 266a, 266b of jaws 262, 264 are oriented parallel to resection level 16. The patella clamp 200 is now oriented in place with respect to patella 10 according to the preoperative plan and resection of patella about resection level 16 can commence. Once patella 10 is resected a resection may be further made through the planar resected surface to receive a corresponding peg, for example of the patellar component.

Although the devices and methods described herein are generally described in relation to patella arthroplasty systems, it should be understood that the devices and methods are not intended to be so limited and could be used with other bone and joints, such as other ball and socket joints, including the ankle, shoulder or hip, for example.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

The invention claimed is:

1. A patella clamp comprising:
   first and second jaw members defining first and second jaw positions of the patella clamp on the patella bone, the first and second jaw positions being located superiorly to a patellar resection plane;
   an actuation member coupled to the first and second jaw members for moving the first and second jaw members along a plane toward and away from one another;
   a tracker capable of receiving and transmitting digital information including a three-dimensional model of an unresected patella bone, wherein the tracker is configured to define the position of the patella clamp on the unresected patella bone based on the three-dimensional model; and
   an adjustable stylus for contacting an articular high point of the patella bone,
   wherein the tracker and adjustable stylus are coupled to the patella clamp, the adjustable stylus being both linearly and rotatably adjustable.

2. The patella clamp of claim 1, wherein the first and second jaw members each have at least one tooth for engaging the patella bone.

3. The patella clamp of claim 1, further comprising first and second parallel support members coupled to the actuation member and the first and second jaw members.

4. The patella clamp of claim 1, wherein the tracker is coupled to one of the first and second parallel support members.

5. The patella clamp of claim 1, wherein the digital information further includes information relating to an orientation of the patella clamp with respect to the patella bone.

6. The patella clamp of claim 1, wherein the adjustable stylus is coupled to one of the first and second jaw members.

7. The patella clamp of claim 1, wherein the adjustable stylus is coupled to one of the first and second jaw members via a post, the adjustable stylus being adjustable about the post.

8. The patella clamp of claim 7, wherein the post includes a plurality of grooves for adjusting the stylus about the post.

9. The patella clamp of claim 8, wherein each of the plurality of grooves correspond to a height of the stylus from the patellar resection plane.

10. A patella clamp comprising:
    first and second jaw members defining first and second jaw positions of the patella clamp on the patella bone, the first and second jaw positions being located superiorly to a patellar resection plane;
    an actuation member coupled to the first and second jaw members for moving the first and second jaw members along a plane toward and away from one another;
    a tracker capable of receiving and transmitting digital information including a three-dimensional model of an unresected patella bone, wherein the tracker is configured to define the first and second jaw positions on the unresected patella bone based on the three-dimensional model; and
    an adjustable stylus for contacting an articular high point of the patella bone, the articular high point of the patella bone corresponding to an articular high point of the implant,
    wherein the tracker and adjustable stylus are coupled to the patella clamp, the adjustable stylus being both linearly and rotatably adjustable.

11. The patella clamp of claim 10, wherein the first and second jaw members each have at least one tooth for engaging the patella bone.

12. The patella clamp of claim 10, further comprising first and second parallel support members coupled to the actuation member and the first and second jaw members.

13. The patella clamp of claim 10, wherein the tracker is coupled to one of the first and second parallel support members.

14. The patella clamp of claim 10, wherein the digital information further includes information relating to an orientation of the patella clamp with respect to the patella bone.

15. The patella clamp of claim 10, wherein the adjustable stylus is coupled to one of the first and second jaw members.

16. The patella clamp of claim 10, wherein the adjustable stylus is coupled to one of the first and second jaw members via a post, the adjustable stylus being adjustable about the post.

17. The patella clamp of claim 16, wherein the post includes a plurality of grooves for adjusting the stylus about the post.

18. The patella clamp of claim 17, wherein each of the plurality of grooves correspond to a height of the stylus from the patellar resection plane.

19. A patella clamp comprising:

first and second jaw members defining first and second jaw positions of the patella clamp on the patella bone, the first and second jaw positions being located superiorly to a patellar resection plane corresponding to a bone contacting surface of the implant;

an actuation member coupled to the first and second jaw members for moving the first and second jaw members along a plane toward and away from one another;

a tracker capable of receiving and transmitting digital information including a three-dimensional model of an unresected patella bone, wherein the tracker is configured to define the first and second jaw positions of the patella clamp based on the three-dimensional model; and an adjustable stylus for contacting an articular high point of the patella bone, the articular high point of the patella bone corresponding to an articular high point of the implant, wherein the tracker and adjustable stylus are coupled to the patella clamp, the adjustable stylus being both linearly and rotatably adjustable.

\* \* \* \* \*